US007695814B2

(12) United States Patent
Gartstein et al.

(10) Patent No.: US 7,695,814 B2
(45) Date of Patent: Apr. 13, 2010

(54) RESPONSIVE COATED PARTICLES COMPARING HYDROPHOBIC AND HYDROPHILIC POLYMERS

(75) Inventors: Vladimir Gartstein, Mason, OH (US); David S. Salloum, Hamilton, OH (US); Faiz Feisal Sherman, Mason, OH (US); Robert Mikhailovych Lupitskyy, Potsdam, NY (US); Sergiy Minko, Potsdam, NY (US); Mikhail Motornov, Potsdam, NY (US); Roman Bogdanovych Sheparovych, Potsdam, NY (US)

(73) Assignee: The Procter & Gamble Company, Cincinnati, OH (US)

( * ) Notice: Subject to any disclaimer, the term of this patent is extended or adjusted under 35 U.S.C. 154(b) by 153 days.

(21) Appl. No.: 11/705,836

(22) Filed: Feb. 14, 2007

(65) Prior Publication Data

US 2007/0190327 A1 Aug. 16, 2007

Related U.S. Application Data

(60) Provisional application No. 60/773,046, filed on Feb. 14, 2006.

(51) Int. Cl.
*B32B 5/16* (2006.01)
*B32B 9/04* (2006.01)

(52) U.S. Cl. ....................... 428/407; 428/447; 525/474; 525/478

(58) Field of Classification Search ................. 428/407, 428/447; 525/474, 478
See application file for complete search history.

(56) References Cited

U.S. PATENT DOCUMENTS

| | | | | |
|---|---|---|---|---|
| 4,715,986 | A * | 12/1987 | Gruning et al. | 516/100 |
| 5,672,297 | A | 9/1997 | Soane | |
| 5,939,485 | A * | 8/1999 | Bromberg et al. | 524/556 |
| 5,997,748 | A | 12/1999 | Rosenberg et al. | |
| 6,254,634 | B1 | 7/2001 | Anderson et al. | |
| 6,435,665 | B2 | 8/2002 | Lerat et al. | |
| 6,451,895 | B1 | 9/2002 | Topolkaraev et al. | |
| 6,855,773 | B1 | 2/2005 | Jensen et al. | |
| 6,967,059 | B2 * | 11/2005 | Sanada et al. | 428/405 |
| 7,020,355 | B2 | 3/2006 | Lahann et al. | |
| 7,572,844 | B2 * | 8/2009 | Sato et al. | 523/160 |
| 2002/0106513 | A1 | 8/2002 | Matyjaszewski et al. | |
| 2003/0194555 | A1 | 10/2003 | Campbell et al. | |

FOREIGN PATENT DOCUMENTS

| | | | |
|---|---|---|---|
| EP | 0 608 274 | B1 | 12/1996 |
| EP | 0 748 342 | B1 | 10/2001 |
| EP | 1 350 575 | A2 | 10/2003 |
| WO | WO 2004/096422 | A1 | 11/2004 |

OTHER PUBLICATIONS

Draper, J., et al., "Mixed Polymer Brushes by Sequential Polymer Addition: Anchoring Layer Effect," *Langmuir*, 2004, vol. 20, pp. 4064-4075.

Minko, S., et al., "Environment-Adopting Surfaces with Reversibly Switchable Morphology," *Macromol. Rapid Commun.*, 2001, vol. 22, pp. 206-211.

Ionov, L., et al., "Gradient Mixed Brushes: 'Grafting To' Approach," *Macromolecules*, 2004, vol. 37, pp. 7421-7423.

Sidorenko, AL., et al., "Switching of Polymer Brushes," *Langmuir*, 1999, vol. 15, pp. 8349-8355.

Uhlmann, P., et al., "Surface functionalization by smart coatings: Stimuli-responsive binary polymer brushes," *Progress in Organic Coatings*, 2006, vol. 55, pp. 168-174.

Zhao, B., et al., "Polymer brushes: surface-immobilized macromolecules," *Prog. Polym. Sci.*, vol. 25, 2000, pp. 677-710.

Ionov, L., et al., "Reversible Chemical Patterning on Stimuli-Responsive Polymer Film: Environment-Responsive Lithography," *J. Am. Chem. Soc.*, 2003, vol. 125, pp. 8302-8306.

Uhlmann, P., et al., "Surface functionalization by smart binary polymer brushes to tune physico-chemical characteristics at biointerfaces," *e-Polymers*, 2005, Vo. 75, pp. 1-10.

Lupitskyy, R., et al., "From Smart Polymer Molecules to Responsive Nanostructured Surfaces," *Langmuir*, 2005, vol. 21, pp. 8591-8593.

Riskin, M., et al., "Switchable Surface Properties through the Electrochemical or Biocatalytic Generation of $Ag^0$ Nanoclusters on Monolayer-Functionalized Electrodes," *J. Am. Chem. Soc.*, 2006, vol. 128, pp. 1253-1260.

Kohut, A., et al., "Design of a New Invertible Polymer Coating on a Solid Surface and Its Effect on Dispersion Colloidal Stability," *Langmuir*, 2006, vol. 22, pp. 6498-6506.

Ketelson, H. A., et al., "Sterically Stabilized Silica Colloids: Radical Grafting of Poly(methyl methacrylate) and Hydrosilylative Grafting of Silicones to Functionalized Silica," Polymers for Advanced Technologies, vol. 6, 1995, pp. 335-344.

Zhang, M. et al., "Double-responsive polymer brushes on the surface of colloid particles," *Journal of Colloid and Interface Science*, vol. 301, 2006, pp. 85-91.

Yang, J. et al., "The Preparation and Surface Properties of Silicone-grafted Acrylic Copolymer Coatings," *High Performance Polymers*, 2005, vol. 17, pp. 85-102.

Yoshihara, T., "Dispersion of surface-modified ultrafine particles by use of hydrophobic monomers," *International Journal of Adhesion & Adhesives*, vol. 19, 1999, pp. 353-357.

Jiang, B., et al., "Surface Modification on Nanoscale Titanium Dioxide by Radiation: Preparation and Characterization," Journal of Applied Polymer Science, vol. 100, 2006, pp. 3510-3518.

Akiva, U., et al., "New micrometer-sized monodispersed self-assembled amphiphilic polystyrene/poly(*n*-butyl methacrylate) composite particles of hemispherical morphology: synthesis and characterization," *Colloids and Surfaces A: Physicochem. Eng. Aspects*, vol. 253, 2005, pp. 9-13.

PCT International Search Report, Jul. 25, 2007, 5 pages.

U.S. Appl. No. 11/705,837, filed Feb. 14, 2007, Gartstein et al.

* cited by examiner

*Primary Examiner*—H. (Holly) T Le
(74) *Attorney, Agent, or Firm*—John M Howell; Leonard W Lewis

(57) ABSTRACT

A responsive coated particle comprising at least one particle comprising an interfacial surface to which a responsive coating attaches, said responsive coating comprising (a) at least one silicone-based, substantially hydrophobic polymer and (b) at least one substantially hydrophilic polymer wherein said responsive coating particle is in a first state.

13 Claims, No Drawings

RESPONSIVE COATED PARTICLES COMPARING HYDROPHOBIC AND HYDROPHILIC POLYMERS

CROSS REFERENCE TO RELATED APPLICATION

This application claims the benefit of U.S. Provisional Application No. 60/773,046, filed Feb. 14, 2006.

FIELD OF THE INVENTION

The present invention relates to a responsive coating provided over the interfacial surface of a particle. Particularly, the invention relates to a responsive coating comprising at least one substantially hydrophobic and at least one substantially hydrophilic polymer formed on a particle's interfacial surface. More particularly, the invention relates to a responsive coating that can switch from a first state to at least a second state, e.g., from a substantially hydrophilic state to a substantially hydrophobic state, upon exposure to an external stimulus, a change in an environmental condition, or time.

BACKGROUND OF THE INVENTION

Interactions at the solid/liquid interface, such as protein adsorption, cell adhesion, and bio-fouling, may be determined by the outermost surface of a substrate. In order to improve a product's interfacial properties, it is desirable to enhance or prevent wetness attributes associated with a particular substrate. For example, it has been desirable to advance technologies concerning wettability properties of particular products such as feminine care and incontinence articles, baby care products, fabric care products and generally, disposable articles in order to improve comfort. Many techniques have been employed to address these concerns but have failed to provide a commercially viable substrate that provides a diverse use within consumer care products.

For example, the Nanopin film was developed around 2005 possessing highly unusual hydrophobic properties. Such technology is characterized as having a "Lotus-Effect" whereby the surface exhibits a hydrophobic characteristic, i.e., extremely poor wettability characteristics and high liquid contact angles. A droplet of water that contacts the surface of the Nanopin film forms an almost perfect sphere with a wet contact angle of approximately 178°.

While hydrophobic surfaces such as Nanopin film may offer a number of commercial advantages, coating a surface of a substrate to provide such hydrophobic conditions fails to address the commercially viable concerns of being useful for a diverse array of uses. For example, it may be desirable to form or coat a surface to exhibit hydrophilic properties in a first instance but, upon application of an external stimulus, can switch to exhibit hydrophobic properties in a second instance. Another example may include the desire to form or coat a surface to exhibit hydrophobic properties in a final instance but requires the coating to be in an initial hydrophilic state in order to allow for a substance to disperse in an aqueous medium. Without being bound by theory, a consumer may desire a liquid solution, comprising hydrophilic particles, to be applied over a household surface for the purposes of cleaning. Upon deposition and drying, the hydrophilic particles may switch from the first hydrophilic state to a second hydrophobic state in order to prevent bio-foul matter such as biological fluid from adhering to the surface.

In order to enhance the wetness properties of a substrate for commercial use as shown above, there must be a teaching that allows for such occurrence of switching between hydrophilic and hydrophobic states, particularly upon application of an external stimulus and/or change in an environmental condition. Since the prior art fails to disclose such structures, much less methods of forming them, the present invention overcomes such deficiencies and shortcomings by the particles disclosed herein.

SUMMARY OF THE INVENTION

The present invention relates to a responsive coated particle comprising at least one particle comprising an interfacial surface to which a responsive coating attaches, said responsive coating comprising (a) at least one silicone-based, substantially hydrophobic polymer and (b) at least one substantially hydrophilic polymer wherein said responsive coating particle is in a first state.

DETAILED DESCRIPTION OF THE INVENTION

While the specification concludes with the claims particularly pointing out and distinctly claiming the invention, it is believed that the present invention will be better understood from the following description.

All percentages, parts and ratios are based upon the total weight of the compositions of the present invention, unless otherwise specified. All such weights as they pertain to listed ingredients are based on the active level and, therefore; do not include solvents or by-products that may be included in commercially available materials, unless otherwise specified. The term "weight percent" may be denoted as "wt. %" herein. Except where specific examples of actual measured values are presented, numerical values referred to herein should be considered to be qualified by the word "about".

All molecular weights as used herein are weight average molecular weights expressed as grams/mole, unless otherwise specified.

As used herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

The term "substrate" as used herein refers to any organic, inorganic, synthetic, or non-synthetic surface. Examples of a substrate include, but are not limited to, a semiconductor wafer, skin, tissue, hard and soft surfaces, cells, woven and non-woven materials, hair, clothing, textiles, and combinations thereof.

The term "particles" is understood as a single particle or an aggregate of particles.

The term "interfacial surface" as used herein refers to any region that separates a single or multi-phases. Such multi-phases include, but are not limited to, solid-liquid phase, liquid-gas phase, solid-gas phase, and solid-solid phase. While the interfacial surface of the present invention is directed to a solid-gas phase, it is understood that other phases will suffice when present.

The present invention relates to a responsive coating on a part or on the entire surface of a particle. The responsive coating is comprised of two or more polymers attached to the interfacial surface of a particle. Such particle may be used to interact with the interface of a substrate wherein wettability properties may be enhanced.

Particles of the present invention may be soft, hard, organic, inorganic, or mixtures thereof and may be selected from the group consisting of oxides, metals, and metal alloys. For example, hard, inorganic particles of the present invention may include, but are not limited to, aluminum oxide, magnesium oxide, iron, iron oxide, titanium dioxide, silica, zinc, zinc iron oxide, zinc oxide. Soft, organic particles of the present invention may include, but are not limited to, dendrimers with surface groups such as poly(amidoamine) (PAMAM) phosphorous, and polypropylenimine; silsesquioxane polymers; polystyrene; polymethyl methacrylate; polyethylene; nylon; melamine (polymethylenemelamine); polyactide; dextran; and chitosan. Particles of the present invention may be selected according to their Young's Modulus value (GPa). Particles of the present invention may have a Young's Modulus value of from about 0.01 GPa to about 1000 GPa. Soft, organic particles of the present invention may have Young's Modulus value of from about 0.01 to about 10 GPa. Hard, inorganic particles of the present invention may have Young's Modulus value of from about 50 GPa to about 1000 GPa.

The responsive coated particles should be small enough so as to minimize interference with visual surface attributes of a substrate to which it may adhere. Therefore, the particles may have a size from about 1 nm, from about 10 nm, from about 20 nm, or from about 50 nm and no more than about 1 μm, no more than about 500 nm, no more than 250 nm, or no more than about 100 nm. The particles may also be round, platelets, elliptical, spherical, cylindrical, tubular, or irregular in shape.

The polymers of the present invention may be substantially hydrophobic, substantially hydrophilic, substantially oleophobic, substantially oleophilic, or mixtures thereof. Substantially hydrophobic polymers of the present invention may be selected from silicone groups, flouro groups, or mixtures thereof. Particularly, the silicone-based, substantially hydrophobic polymers of the present invention may comprise siloxane polymers, specifically polydimethylsiloxane (PDMS) or aminopropyl-terminated PDMS. Substantially hydrophilic polymers of the present invention may be a polyelectrolyte, specifically polyethylenimine (PEI). Particularly, substantially hydrophilic polymers may be selected from the group consisting of polyethylene oxide and its derivatives, polyacrylamide and its derivatives, poly alkyl (acrylic) acid and its salts, polystyrene sulfonic acid and its salts, and mixtures thereof. The polymers may be attached to the particle in varying amounts. For example, 70% of the substantially hydrophobic polymers may comprise PDMS while the remaining 30% of the substantially hydrophilic polymers may comprise PEI.

Without being bound by theory, the responsive coating of the present invention may comprise polydimethylsiloxane (PDMS) as the substantially hydrophobic polymer. PDMS has a glass transition temperature (Tg) of approximately negative 125° C. (−125° C.), and a melting point (Tm) of approximately negative 40° C. (−40° C.). PDMS has very flexible siloxane bonds and the Tg of PDMS allows additional flexibility in the design and modification of the PDMS backbone. For instance, functional polymers may be added to the PDMS backbone changing the Tg of PDMS. PDMS also has higher permeability to gases than most other elastomeric materials. One important feature that PDMS provides is very low surface energies that are produced from the silicone polymeric surface. PDMS has a surface energy of approximately 20 dyne/cm. Polyethylenimine (PEI) may be selected as the substantially hydrophilic polymer due to its availability and good solubility at the desired pH. It provides the reactive groups (amine groups) for grafting to a particle surface.

The mass ratio of substantially hydrophobic polymers to substantially hydrophilic polymers may be greater than about 0.01, greater than about 0.05, greater than about 1.0, greater than about 2.0 or less than about 100, less than about 50.0, less than about 10.0, less than about 8.0, or less than about 2.0. For example, the mass ratio of substantially hydrophobic polymers to substantially hydrophilic polymers may be from about 0.01 to about 100.

The polymers of the present invention attach to the interfacial surface of a particle to form a responsive coating by means of grafting. The combination of particular elements such as the selection of polymers, the functional groups that attach to the selected polymers, and the mass ratio of the polymers are amongst various factors for programming the responsive coating of the particles of the present invention. By "programming", it is meant that the responsive coating is set by the aforementioned factors to exist in a particular state such as substantially hydrophobic, substantially hydrophilic, substantially oleophobic, substantially oleophilic, or mixtures thereof. The "first state" is considered as the first state that the particle exists. The states may succeed accordingly (second state, third state, etc . . . ) thereafter. The term "responsive" is used to describe the behavior of the coated particle when exposed to a external stimulus including, but not limited to, environment, pH, polarity, temperature, and substrate surface (texture, type (solid, liquid, gas), material, etc . . . ). The particles may be deposited on a substrate wherein the substrate will exist in a particular first state. Due to the presence of the particles on the substrate, the substrate will respond to any external stimulus to provide advantageous wettability properties.

Without being bound by theory, responsive coated particles may comprise a coating comprising PDMS and PEI wherein due to the substantially hydrophilic polymers (PEI), the coating allows the particles to be substantially in a hydrophilic first state. When a composition comprising such particles is exposed to an external stimulus such as heat, the particles may "respond" by switching from the substantially hydrophilic first state to a substantially hydrophobic second state. These particles may be further exposed to an acidic solution with a pH of about 5.5 wherein the particle may again "respond" by switching from the substantially hydrophobic second state to a substantially hydrophilic third state.

Particles of the present invention may also be subject to reversion as part of the response or switch from one state to another. For example, a composition comprising the substantially hydrophobic particles of the present invention may be exposed to an external stimulus such as UV, pH or temperature causing the particles to switch from the first substantially hydrophobic state to a second substantially hydrophilic state. After a period of time, the particles may revert back to a substantially hydrophobic state without additional exposure to an external stimulus.

Thus, a particle of the present invention may remain in a particular state until exposure to an external stimulus. Time, however, may also act as an intentional or unintentional factor that acts as a trigger to cause the particles to switch. The response of the particles is, however, determinable by their programming. Such behavior is exemplary of the coating and thus, the responsive coated particle of the present invention.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1

Silica nanoparticles (particle size: 0.014μ, surface area: 200±25 $m^2$/g) were dried in vacuum oven at 120° C. for 12 h and then immediately used for silanization (see below). 1 g of silica particles were dispersed in 200 mL of toluene in an ultrasonic bath for 2 h. 2 mL of GPS (3-(glycidoxipropyl) trimethoxysilane) was added to the dispersion and the mixture was stirred for 12 h at room temperature. Afterward, the particles were isolated from the silanization mixture by centrifugation, re-dispersed in toluene, and centrifuged again. This washing process was repeated with toluene one more time. After the final centrifugation the particles were re-dispersed in MEK (methyl ethyl ketone) with the concentration of the particles of 1%. In the next step, GPS modified particles (20 ml of 1% dispersion in MEK) were mixed with 4 g of PDMS (polydimethylsiloxane with amino end functional group, Mw 30K) followed by evaporation of the solvent at the temperature lower than 50° C. The polymer-particles mixture was divided into three parts. The mixtures were heated in vacuum oven at 90° C. for 3 h (Sample#1), 80° C. for 1 h (Sample#2), and 70° C. for 1 h (Sample#3) to achieve three different grafting densities of PDMS layers. The particles were isolated by centrifugation, re-dispersed in MEK, and centrifuged again. This washing process was repeated three times to remove non-grafted PDMS. The grafting of PEI (polyethyleneimine, Mw 25K) was performed in the same way as the grafting of PDMS. The grafting temperature was 90° C. with the grafting time of 3 h for each sample. After removal of non-grafted PEI, the particles were dispersed in water at pH 2. Then pH of the mixture was adjusted to pH 5 by adding a solution of NaOH. The modified switchable particles finally exist in an aqueous dispersion.

Example 2

The synthetic procedure starts with the covalent grafting of GPS onto the polymethylsilsesquioxane particles (300 nm), followed by the consequent grafting of poly(dimethylsiloxane) (PDMS) and polyethyleneimine (PEI). 0.4 mL of GPS was added to a 40 mL solution of 1% particle dispersion in methyl ethyl ketone (MEK) and the mixture was stirred for 12 hours at room temperature. Afterward, the particles were isolated from the silanization mixture by centrifugation, re-dispersed in the MEK and centrifuged again. This washing process was repeated three more times. In the next step, the GPS-modified particles (40 mL of 1% dispersion in the MEK) were mixed with 10% poly(dimethylsiloxane), aminopropyl terminated (Mw 30000). The mixture was heated in a water bath at 70° C. for 6 hours while being vigorously stirred. After that, the dispersion was washed of its unreacted polymer by the centrifugation process described above. PDMS-grafted particle dispersion (1% in MEK) was divided into four parts. Each part was mixed with water free, PEI (Mw 25000) at a concentration of 10% by weight. The mixtures were heated in a water bath at 70° C. while being vigorously stirred for a variety of times in order to achieve different PEI layer grafting densities. The particles were washed of unreacted PEI by the centrifugation process described above and then dispersed in Millipore water containing 1% solids by weight.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the term in a document incorporated herein by reference, the meaning or definition assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A responsive coating for a particle wherein the coating comprises:

c. at least one silicone-based, substantially hydrophobic polymer and d. at least one substantially hydrophilic polymer wherein upon coating the particle, the polymers attach to the interfacial surface of the particle allowing said particle to be programmed to exist in a first state where upon exposure to an external stimulus, the particle responds and is transformed from its first state to a second and distinguishable state.

2. The responsive coating of claim 1 wherein the substantially hydrophobic silicone-based polymers comprise PDMS.

3. The responsive coating of claim 2, wherein the mass ratio of the silicone-based, substantially hydrophobic polymer to the substantially hydrophilic polymer is greater than 0.05 and less than about 10.0.

4. The responsive coating of claim 1 wherein the substantially hydrophilic polymers comprise PEI.

5. The responsive coating of claim 4, wherein the mass ratio of the silicone-based, substantially hydrophobic polymer to the substantially hydrophilic polymer is greater than 0.05 and less than about 10.0.

6. A particle comprising the responsive coating of claim 1 and a particle size from about 1 nm to about 1 μm.

7. The particle of claim 6 wherein the first state is hydrophilic.

8. The particle of claim 6 wherein the particle has a Young's Modulus value of from about 0.01 GPa to about 1000 GPa.

9. The particle of claim 8 wherein said particle is a soft, organic particle with a Young's Modulus value of from about 0.01 GPa to about 10 GPa.

10. The particle of claim 8 wherein said particle is a hard, inorganic particle with a Young's Modulus value of from about 50 GPa to about 1000 GPa.

11. A method of switching the response coating for a particle of claim 1 from a first state to at least a second state comprising the step of exposing the particle to at least one external stimulus to create a transformation wherein said particle resides in a second state other than said first state.

12. The method of claim 11 wherein said particle reverts from said second state to said first state without exposure to additional stimulus.

13. The method of claim 12 wherein said particle is exposed to an additional external stimulus to cause the particle residing in a second state to reside in a third state other than said first and second states.

* * * * *

UNITED STATES PATENT AND TRADEMARK OFFICE

CERTIFICATE OF CORRECTION

PATENT NO. : 7,695,814 B2
APPLICATION NO. : 11/705836
DATED : April 13, 2010
INVENTOR(S) : Vladimir Gartstein et al.

It is certified that error appears in the above-identified patent and that said Letters Patent is hereby corrected as shown below:

Cover Page

In the title (54), and col. 1, line 2, delete "COMPARING" and insert --COMPRISING--.

Column 6

Line 22, delete "c." and insert --a.--.

Line 24, delete "d." and insert --b.--.

Signed and Sealed this
Eleventh Day of January, 2011

David J. Kappos
*Director of the United States Patent and Trademark Office*